Figure 1:
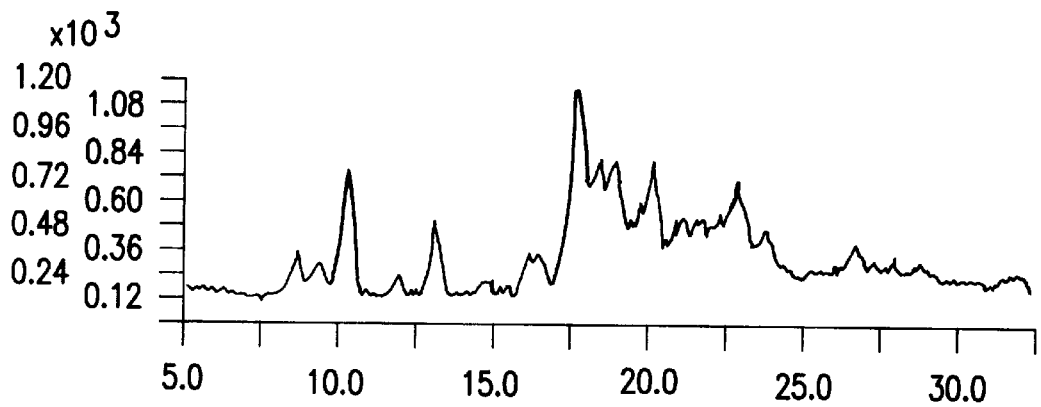

United States Patent [19]

Bosone et al.

[11] Patent Number: 5,808,069
[45] Date of Patent: Sep. 15, 1998

[54] SALTS OF 2-(3-BENZOYLPHENYL) PROPIONIC ACID WITH ORGANIC BASES AND PHARMACEUTICAL COMPOSITIONS THEREOF

[75] Inventors: Enrico Bosone; Gaetano Clavenna; Carmelo Gandolfi; Marco Mantovanini; Roberto Curti, all of Milan, Italy

[73] Assignees: Dompe' Farmaceutici SpA, Milan; Dimpe' SpA, L'Aquila, both of Italy

[21] Appl. No.: 513,842
[22] PCT Filed: Mar. 7, 1994
[86] PCT No.: PCT/IT94/00020
§ 371 Date: Oct. 31, 1995
§ 102(e) Date: Oct. 31, 1995
[87] PCT Pub. No.: WO94/20449
PCT Pub. Date: Sep. 15, 1994

[30] Foreign Application Priority Data

Mar. 9, 1993 [IT] Italy .............................. MI93 A 000447
Feb. 25, 1994 [IT] Italy .............................. MI94 A 000348

[51] Int. Cl.$^6$ .................. C07C 59/84; C07C 229/26; C07D 295/08
[52] U.S. Cl. .................. 544/394; 562/560; 562/561; 562/562
[58] Field of Search ............... 544/394; 562/560, 562/561, 562; 514/255, 570

[56] References Cited

U.S. PATENT DOCUMENTS

| 4,279,926 | 7/1981 | Bruzzese et al. | 424/316 |
| 5,089,405 | 2/1992 | Cerbelaud et al. | 435/136 |
| 5,097,064 | 3/1992 | Grosselin | 562/401 |
| 5,331,000 | 7/1994 | Young et al. | 514/570 |

FOREIGN PATENT DOCUMENTS

| 882 889 | 8/1980 | Belgium . |
| 0 502 502 | 9/1992 | European Pat. Off. . |
| 92/18455 | 10/1992 | WIPO . |

*Primary Examiner*—Mukund J. Shah
*Assistant Examiner*—Deepak R. Rao
*Attorney, Agent, or Firm*—Nikaido, Marmelstein, Murray & Oram LLP

[57] ABSTRACT

The salts of S(+) 2-(3-benzoylphenyl)propionic acid and of R(-) 2-(3-benzoylphenyl)propionic acid with an organic base such as D-lysine, L-lysine, L-arginine, (R) 3-(4-phenylpiperazin-1-yl)propane-1,2-diol and (S) 3-(4-phenylpiperazin-1-yl)propane-1,2-diol, the process for their preparation and the corresponding pharmaceutical compositions containing said salts are described.

5 Claims, 1 Drawing Sheet

SALTS OF 2-(3-BENZOYLPHENYL) PROPIONIC ACID WITH ORGANIC BASES AND PHARMACEUTICAL COMPOSITIONS THEREOF

DESCRIPTION

Salts of 2-(3-benzoylphenyl)propionic organic bases and pharmaceutical compositions thereof

TECHNICAL FIELD

The object of the present invention relates to salts of 2-(3-benzoylphenyl)propionic acid with achiral and chiral organic bases, and to the pharmaceutical compositions containing them.

A further object of the invention relates to the process for the preparation of said salts.

More particularly, the present invention relates to the salts of the S(+) and R(−) enantiomers of 2-(3-benzoylphenyl) propionic acid with achiral amine, such as, for example, tris-(hydroxymethyl)aminomethane, also known as tromethamine, and with chiral amine such as, for example (R) and (S) 3-(4-phenylpiperazin-1-yl)propane-1,2-diol, also known as dextrodropropizine and levodropropizine, and with basic α-aminoacids such as, for example, D-lysine, L-lysine and L-arginine, all salts which may be separated as single chemical individuals of high optical purity.

BACKGROUND OF THE INVENTION

Because of its high tolerability, the (S,R) (±) 2-(3-benzoylphenyl)propiornic acid, also known as ketoprofen, is one of the non-steroidal anti-inflammatories of widespread use in clinics, both for the treatment of serious inflammatory conditions and for its use as an anagelsic and antipyretic. Pharmaceutical compositions of current use containing ketoprofen, have racemate as its active principle, where the two enantiomers S(+) and R(−) are present in equimolecular ratio between themselves.

The active principle is normally used as free acid, practically insoluble in water, in pharmaceutical compositions destined for oral use, while for alternative ways of administration, for example that of parenteral administration, adaptable ketoprofen salts with organic and inorganic bases are used.

In the past, all the pharmacological activities peculiar to the racemate of 2-arylpropionic chiral acid, were thought to be constitutive of the enantiomer S(+) which only was found to inhibit the endogenous synthesis of the pro-inflammatory algogene and pirogene prostaglandines, in which respect the antipode R(−) is inactive or practically so. On the other hand, it is well known that the R(−) enantiomer of the 2-arylpropionic acids undergoes, to a variable extent and in a way animal species dependent, metabolic epimerization in the S(+) enantiomer, an event which, for a long time, has prevented a correct characterization of the pharmacological properties of the individual enantiomers.

Only recently, using flurbiprofen, a chiral 2-arylpropionic anti-inflammatory and analgesic acid, whose enantiomers are not metabolically converted one into another, K. Brune et al. (Experientia, 47, 257, 1991) have clearly shown that the inhibition of the prostaglandine synthesis mainly mediates the anti-inflammatory activity of the compound, while mechanisms independent from the inhibition of the prostaglandine synthesis contribute to the analgesic effects of the racemate. Of the two antipodes, the S(+) form inhibits the prostaglandine synthesis, the inflammation and the perception of the pain, while the R(−) antipode, which has much less effect on the inhibition of the prostaglandine synthesis and has no effect on the inflammation, blocks the perception of the pain with a potency rather similar to that of the antipode S(+).

S(+) flurbiprofen is clearly ulcerogenic for the gastroenteric mucose, unlike the R(−) enantiomer. On the basis of these results, the A.A.s conclude on the existence of additional mechanisms of analgesia and propose a new and correct therapeutic use of the R(−) 2-arilpropionic acids as analgesics.

These concepts are further charactered in a successive article (K. Brune et al., J. Clin, Pharmacol., 32, 944, 1992) where it is concluded that, having recourse to the use of individual enantiomers of the chiral 2-arylpropionic acids instead of the racemate, it is possible:

a) to reduce the dose and by that the metabolic load;
b) to reduce the variability in clinical response by eliminating the biochemical inversion pathway;
c) to reduce compliance problems due to unnecessarily high doses;
d) to establish more specific drug treatment (R-enantiomers in occasional pain, S-enantiomers in rheumatic disorders).

DESCRIPTION OF THE INVENTION

The object of the present invention relates to pharmacologically active salts of 2-(3-benzoylphenyl)-propionic acid with achiral and chiral organic bases and to the process of their preparation and to the pharmaceutical compositions containig them.

More particularly those are salts of the enantiomeric forms S(+) and R(−) of the 2-(3-benzoylphenyl)propionic acid with achiral amines such as, for example, tris (hydroxymethyl)aminomethane, also known as tromethamine, and with chiral amines such as, for example, (R) and (S) 3-(4-phenylpiperazin-1-yl)proparne-1,2-diol, also known as dextrodropropizine and levodropropizine, and with basic α-aminoacids such as, for example, D-lysine, L-lysine and L-arginine, salts which may all be isolated as single chemical individuals having high optical purity.

The salts of S(+) 2-(3-benzoylphenyl)propionic acid with the above-mentioned bases are in particular usefully employed in the treatment of those pathological symptoms of rheumatoid and cronic type, which require the drug to be administered at high dosage, continuously and for long periods of time.

In such event, the presence in the racemic form of the enantiomer R(−), which is ineffective as an inflammatory drug, would represent for the patient an unnecessary metabolic load which would even be harmful. In fact the optical antipode R(−), which is pharmacologically inactive in inhibiting the prostaglandine synthesis, and therefore as anti-inflammatory agent, does not or only very slightly and in a kinetically and therapeutically inefficient way, undergo epimerization in man to the enanliomeric form S(+) to which the anti-inflammatory activity of the racemate are due.

The salts of the R(−) 2-(3-benzoylphenyl)propionic acid with the above-mentioned bases are in particular usefully employed in treating acute painful symptoms of spastic type (renal, biliary or hepatic colics) and/or tissue-type characterized by sensibilization of the nerve ends and/or of traumatic type.

More generally and in some situations of acute pain, the same compounds could be proposed as a true alternative to the use of narcotics.

It is important and desirable that for the treatment of acute and very painful manifestations, there are pharmaceutical compositions suitable for immediate use and manageable, which rapidly release the active principle and are of high bio-availability.

Typical examples of these compositions are those by parenteral administration and/or by oral administration which are drinkable, which allow a fine dispersion of the active principle. Due to the scarce solubility in water of the active principle, it is necessary to resort, for these purposes, to the use of salts, as single chemical individuals or obtained by extemporary salification during the pharmaceutical formulation process.

Salts of phenylalkylenecarboxylic acids with basic aminoacids, among which ketoprofen lysine salt is cited, are described in DE -A- 25 08 895 and the L-lysine salt of ketoprofen is described in BE -A-882 889.

Pharmaceutical formulations are known which contain salts of racemic ketoprofen and those containing sodium salt (ketoalgine$^R$) and D,L-lysine salts (Artrosilene$^R$) are of current use.

More recently, in patent applications WO 93/16689 (2802, 1992) and WO 93/17677 (09.03.1992) relating to the use of R(−) ketoprofen as an analgesic, pharmaceutical compositions containing as active principle R(−) ketoprofen or a salt thereof with pharmaceutically acceptable organic and inorganic non-toxic bases, are indicated. In both cases, a general reference is made to addition salts of R(−) ketoprofen with various metal ions among which those with alkaline and earth-alkaline metals and with various organic bases, among which the salts with the basic amino acids, such as lysine and arginine.

While the salification process of a chiral 2-arylpropionic acid, in the racemic form, does not involve problems concerning the chemical racemizations of the active principle, this aspect assumes a noticeable relevance when the salification involves the same chemical species but in their optically active form.

In the latter case, the possibility of an oncoming chemical racemization during the salification, drying and storage processes of the raw material, or successively in a state of solution, or during manipulation of the pharmaceutical formulation, cannot be excluded.

It follows that the salification process, the characteristic of the chemical specie salt, the more appropriate to preserve the integrity of the active principle, are not accessory elements of the manipulation and of the practical utilization of the enantiomerically pure active principle.

The salts of the R(−) 2-(3-benzoylphenyl)propionic acid or R(−) ketoprofen, the salts of the S(+) 2-(3-benzoylphenyl) propionic acid or S(+) ketoprofen with achiral organic bases, such as for example, tromethamine, or with chiral, enantiomerically pure, organic bases, such as L-lysine, D-lysine, L-arginine, (S) 3-(4-phenylpiperazin-1-yl)propane-1,2-diol and (R) 3-(4-phenylpiperazin)-1-yl)propane-1,2-diol have been obtained as single chemical individuals, and form the object of present invention.

The process for preparing the above said salts consists of a salification reaction, in a suitable solvent and kept warm, of one of the above-mentioned bases, with R(−) 2-(3-benzoylphenyl)propionic acid or S(+) 2-(3-benzoylphenyl) propionic acid, having an enantiomeric purity of no less than 95%. After cooling, the corresponding salts separate themselves in a good yield, as such or after re-crystallization, and contain the salifying acid which has an optical purity of no less than 99%.

Preferred solvents used in the salification reaction are alcohols such as methanol, ethanol, propanol and isopropanol; ketones such as acetone; water and /or mixtures containing such solvents.

In the salification process with one of the above mentioned α-aminoacids, specifically in the case of lysine, the solvent more particularly preferred is aqueous isopropanol, in a ratio acid:solvent of 1 to 20, with an average water content of 3%. In these experimental conditions the salification, for example, of the R(−) 2-(3-benzoylphenyl) propionic acid with L-lysine gives crystalline solids which are easily filtered and which, after drying, allow to isolate single crystalline individuals of high purity and stability, which may be characterized by I.R. spectrometry and by diffraction of the powder by X-ray.

The salts of the enantiomers of the S(+) and R(−) 2-(3-benzoylphenyl)propionic acids of the present invention, are stable solids, easily filtered and obtainable during the phase of production or purification. They can be in the form of amorphous solids only apparently crystalline, such as the salts of S(+) ketoprofen with L-arginine and of R(−) ketoprofen with D-lysine, or in the form of a crystalline monohydrate such as the salt of S(+) ketoprofen with D-lysine.

The salt of R(−) ketoprofen with L-lysine is one with a residual humidity of about 1%, which in time does not absorb hydration water, and it keeps itself stable in time and is, therefore, particularly manageable, either as such, or as a pharmaceutical composition in which it is contained.

The enantiomeric forms R(−) and S(+) of the 2-(3-benzoylphenyl)propionic acid, or R(−) and S(+) ketoprofen, of convenient optical purity are obtained by optical resolution of the S,R(±) ketoprofen.

Several processes are known by which the two enantiomeric forms of ketoprofen may be separated: a method based on converting the racemic acid with (-)-cinchonidine and then separating the two enantiomers, in particular the S(+) form of ketoprofen is described in WO92/18455 and a method based on the preparation of diastereomerically pure ketoprofen esters, through which the enantiomeric forms of ketoprofen separate, is described in DE 41 26 859.

In particular, R(−) ketoprofen is preferably obtained through a process which utilizes the salification of (R,S) ketoprofen, at room temperature, with (S) 3-(4-phenylpiperazin-1-yl)propan-1,2-diol in acetone at relatively high dilutions (acid:solvent=1:15). After the filtration of a salt, enantiomerically rich in S(+) ketoprofen and cooling the mother waters to 0° C., the R(−) ketoprofen S(−) 3-(4-phenylpiperazin-1-yl)propane-1,2-diol salt crystallizes, having a highly satisfactory optical purity. As an alternative, the salification at 40° C., in methanol (acid:solvent=1 g:5 ml) with R(+) 3-(4-phenylpiperazin-1-yl)propane-1,2-diol produces crystallization on cooling of the salt R(−) ketoprofen with R(+) 3-(4-phenylpiperazin-1-yl)propane-1,2-diol having an optical purity of about 80%. The desired 98% optical purity is reached by recrystallization from acetone or by successive treatment with S(−) 3-(4-phenylpiperazin-1-yl)propane-1,2-diol in acetone (solute:solvent=1:10).

S(+) 2-(3-benzoylphenyl)propionic acid having enantiomeric purity (o.p.) of no less than 90% is obtained, at first time, by salifying the racemate S,R(±) 2-(3-benzoylphenyl) propionic acid in acetone with R(−) 3-(4-phenylpiperazin-1-yl)propane)1,2-diol. A diastereoisomer salt crystallizes which, after filtration and drying in vacuo, is suspended in water. After acidification of the suspension and extraction with an organic solvent such as, for example, ethyl ether, cyclohexane and/or mixtures thereof, the S(+) 3-(2- benzoylphenyl)propionic acid is obtained with a yield of 60±5%, having an optical purity of at least 90%.

A further improvement in enantiomer yield is obtained by a resolution process that uses salification of the racemic acid with half molecular equivalent of the resolvent (S) or (R)-dropropizine.

In comparison to the known salts in which 2-(3-benzoylphenyl)propionic acid is contained in racemic form, the salts of the present invention show a higher purity degree and a greater stability which positively reflects on the handling of the product as such or as a pharmaceutical preparation containing it. In particular, in the case where the salts are formed with the D- and L-lysine enantiomers, the presence of a certain quantity of crystallization water or humidity allows a higher stability of the products.

Moreover the salts of the invention offer the advantage of allowing the preparation of pharmaceutical compositions, the active principle of which is constituted by diastereoisomerically pure single molecular individualities that, as such, give an absolute consistency of quality even with the changing of the preparation batch.

The salts of the invention may be suitably mixed with pharmaceutically acceptable excipients and formulated in a suitable manner for oral, intranasal, parenteral, topical and inhalant administration. The pharmaceutical compositions, which contain as active principle an effective quantity of one or more salts of the enantiomer S(+) or R(−) 2-(3-benzoylphenyl) propionic acid with an organic achiral base such as tromethamine and/or an organic chiral base selected among L-lysine, D-lysine, L-arginine (S) and (R) 3-(4-phenylpiperazin-1-yl)propane-2,3-diol may be in the form of pills, tablets, dragees, granulates, powders, emulsions, solutions, foams, creams, suppositories and spray.

The quantity of the active principle evaluated as salifying acid which is daily administered may vary depending on the type of the administration chosen, on the age and on the condition of the patient.

In the case of oral administration it varies from 20 to 200 mg which may be divided in several doses or as a long-lasting single dose and, in the case of injectable administration, it varies from 10 to 100 mg which may be divided in several doses. For topical administration concentrations of 1% to 10% are suitable, while in the case of sublingual administration single doses of 10 to 50 mg up to a daily total dose of 200 mg may be administered. For the aerosol administration single doses of 10 to 100 µg up to a daily total dose of a maximum of 800 µg may be administered.

Pharmaceutical formulations suitable for the administration of the salts of the invention as nasal spray in concentration of from 0,1 to 2% and those suitable as colluttory in concentration of from 5 to 15%.

1. Preparation of R(−) 2-(3-benzoylphenyl) propionic acid

To a solution of 400 g (R,S)-2-(3-benzoylphenyl) propionic acid in 8 l acetone are added, under stirring and maintaining the temperature at 20°–25° C. by means of external cooling, 440 g S(−) 3-(4-phenylpiperazin-1-yl) propane-1,2-diol. Stirring is maintained for a further 15 minutes until complete dissolution then the salt is allowed to crystallize. After 6 hours the precipitate is filtered, dried in the air and 370 g (2S,2'S') 3'-(4'-phenylpiperazin-1-yl) propane-1',2'-diol 2-(3-benzoylphenyl)propionate are obtained.

$[\alpha]_D = -2.8°$ (MeOH, o.p.(S) 82%)

The mother waters are concentrated to a volume of 6 l and cooled to 0° C. and separate 280 g (2R,2'S) 3'-(4'phenylpiperazin-1'-yl)propane-1',2'-diol 2-(3-benzoylphenyl)propionate.

$[\alpha]_D = -19.8°$ (MeOH, o.p. (R) 97.98%)

Recrystallization from acetone of the compound (solute:solvent 1:10) gives the enantiomerically pure salt, melting at 107°–109° C.

$[\alpha]_D = -20.8°$ (MeOH)

A suspension of 25 g (2R,2'S) 3'-(4'phenylpiperazin-1'-yl)propane-1',2'-diol 2-(3-benzoylphenyl)propionate in 30 ml water is acidified to pH 1 with 2N sulphuric acid, then twice extracted with 4 ml ethylacetate. The organic phases are collected together, washed with water, made anhydrous on sodium sulphate and evaporated to dryness. By recrystallization of the residue from cyclohexane 11 g R(−) 2-(3-benzoylphenyl)propionic acid, melting at 75°–76° C. are obtained.

$[\alpha]_D = -51°$ (1% in $CH_2 Cl_2$)

2. Preparation of S(+) 2-(3-benzoylphenyl) propionic acid

Grams 22 of (R,S) 2-(3-benzoylphenyl)propionic acid are treated with 20 g of R(+) 3-(4-phenylpiperazin-1-yl) propane1,2-diol in 0.1 l methanol and 18 g of (2R,2'R) 3'-(4'phenylpiperazin-1'-yl)propane-1',2'-diol 2-(3-benzoylphenyl)propionate are obtained.

$[\alpha]_D = +2.9°$ (MeOH, o.p. (R) 80%).

Removing by distillation the solvent and crystallizing the residue from 250 ml acetone, 10 g of (2S,2'R) 3'-(4'-phenylpiperazin-1'-yl)propane-1',2'-diol 2-(3-benzoylphenyl)propionate, are obtained.

$[\alpha]_D = +20°$ (MeOH, o.p. (S) 98%).

The product is dissolved in water and acidified to give S(+) 2-(3-benzoylphenyl)propionic acid melting at 74°–77° C.

$[\alpha]_D = +51.2°$ (1% $CH_2 Cl_2$)

Hereunder are some Examples for a better illustration of the invention.

EXAMPLE 1

R(−) 2-(3-benzoylphenyl)propionic acid L-lysine salt

R(−) 2-(3-benzoylphenyl)propionic acid D-lysine salt

Grams 300 or R(−) 2-(3-benzoylphenyl)-propionic acid are dissolved at room temperature in 3 l of isopropanol.

The solution is heated, under stirring, to 60° C. and a solution of 168 g L-lysine in 160 ml of deionized water are added thereto. The solution is filtered hot, diluted, under stirring, with 3 l of isopropanol and left to cool. When the crystallization begins at 48°–50° C. the stirring is interrupted. Two hours later a crystalline precipitate is filtered, washed with 600 ml isopropanol. It is dried in the air; after sieving on a 500 µsieve it is dried in vacuo at 50° C. (20 mm Hg). Grams 390 of R(−) 2-(3-benzoylphenyl)propionic acid L-lysine salt, melting al, 106°–108° C. are obtained. The X-ray diffraction spectrum is given in FIG. 1, are obtained.

(H$_2$O)K.F.: 1.4%

$[\alpha]_D$=+10.6° (c=1%, MeOH); $[\alpha]_{436}$=+30.4° (c=1% MeOH)

Operating in a similar manner, salifying with D-lysine R(–) 2-(3-benzoylphenyl)propionic acid D-lysine salt melting at 106°–108° C., as amorphous solid was obtained.

$[\alpha]_D$=+1.2° (c=1%, MeOH); $[\alpha]_{436}$=+10.4° (c=1% MeOH)

EXAMPLE 2

R(–) 2-(3-benzoylphenyl)propionic acid tris-hydroxymethylmethylammonium salt

S(+) 2-(3-benzoylphenyl)propionic acid tris-hydroxymethylmethylammonium salt

A solution of 5 g R(–) 2-(3-benzoylphenyl)propionic acid in isopropanol is treated with a solution of 2.4 g of tris-hydroxymethylaminomethane in 2.5 ml deionized water. It is evaporated with great care under vacuo and the oily residue taken up with 20 ml of ethylether. The crystalline solid which is separated is filtered and it gives 5.4 g of R(–) 2-(3-benzoylphenyl)propionic acid tris-hydroxymethylmethylammonium salt, melting at 101°–103° C.

(H$_2$O)K.F.: 2.05%

$[\alpha]_D$=+4° (c=1%, MeOH); $[\alpha]_{436}$=+18.2° (c=1% MeOH)

Operating in a similar manner, by salifying the S(+) 2-(3benzoylphenyl)propionic acid the S(+) 2-(3-benzoylphenyl)propionic acid tris-hydroxymethylmethylammonium salt, melting at 102°–103° C. is obtained.

$[\alpha]_D$=–4.1° (c=1%, MeOH); $[\alpha]_{436}$=–17.4° (c=1% MeOH)

EXAMPLE 3

R(–) 2-(3-benzoylphenyl)propionic acid S(–) 3-(4-phenylpiperazin-1-yl)propane-1,2-diol salt R(–) 2-(3-benzoylphenyl)propionic acid R(+) 3-(4-phenylpiperazin-1-yl)propane-1,2-diol salt By salification of a solution of 1 g of R(–) 2-(3benzoylphenyl)propionic acid in 10 ml acetone heated to 40° C. with S(–) 3-(4-phenylpiperazin-1-yl)propane-1,2-diol and followed by cooling at room temperature a precipitate is separated which is filtered and dried in vacuo at 50° C. (20 mm Hg) and gives R(–) 2-(3-benzoylphenyl) propionic S(–) 3-(4-phenylpiperazin-1-yl)propane-1,2-diol salt melting at 107°–109° C.

$[\alpha]_D$=–20.4° (c=1%, MeOH); $[\alpha]_{436}$=–39.5° (c=1% MeOH)

Operating, in a similar manner, by salifying with R(+) 3-(4-phenylpiperazin-1-yl)propane-1,2-diol, the R(–) 2-(3benzoylphenyl)propionic acid R(+) 3-(4-phenylpiperazin-1-yl)propane-1,2-diol salt melting at 118°–120° C. is obtained.

$[\alpha]_D$=–1.5° (c=1%, MeOH); $[\alpha]_{436}$=–3° (c=1% MeOH)

EXAMPLE 4

R(–) 2-(3-benzoylphenyl)propionic acid L-arginine salt

S(+) 2-(3-benzoylphenyl)propionic acid L-arginine salt

A solution of 0.6 g L-arginine in 1 ml boiling water under gentle stirring is added to a solution of 1.02 g of R(–) 2-(3-benzoylphenyl)propionic acid in 10 ml acetone, heated to 40°–45° C.; a solid is separated which is filtered hot gives 1.3 g of R(–) 2-(3-benzoylphenyl)propionic acid L-arginine salt melting at 75° C.

$[\alpha]_D$=+7.7° (c=1%, MeOH); $[\alpha]_{436}$=–21.3° (c=1% MeOH)

Operating in the same manner, when using the S(+) 2-(3-benzoylphenyl)propionic acid on cooling it separates an oily mass. After separation of the liquid phase, the oily residue is diluted with about 10 ml ethylether, the mass solidifies and is finally dispersed.

The following filtration of the solid gives 1.12 g of S(+) 2-(3-benzoylphenyl)propionic acid L-arginine salt, melting at 85° C.

$[\alpha]_D$=+1.6° (c=1%, MeOH); $[\alpha]_{436}$=–3.7° (c=1% MeOH)

EXAMPLE 5

S(+) 2-(3-benzoylphenyl)propionic acid L-lysine salt .1/4 H$_2$O

Grams 0.28 of L-lysine dissolved at 80° C. in 0.3 ml of distilled water are added to a solution of 0.5 g S(+) 2-(3-benzoylphenyl)propionic acid (o.p.>90%; $[\alpha]_D$=+50° in dichloromethane) in 10 ml isopropil alcohol, heated at 40° C.

The so obtained solution is left under stirring; for cooling, an oil is separated which, while it solidifies, is dispersed under stirring, forming a fine crystalline powder. The precipitate is filtered, first washed with isopropyl alcohol and then with ethyl alcohol.

Figure 2:
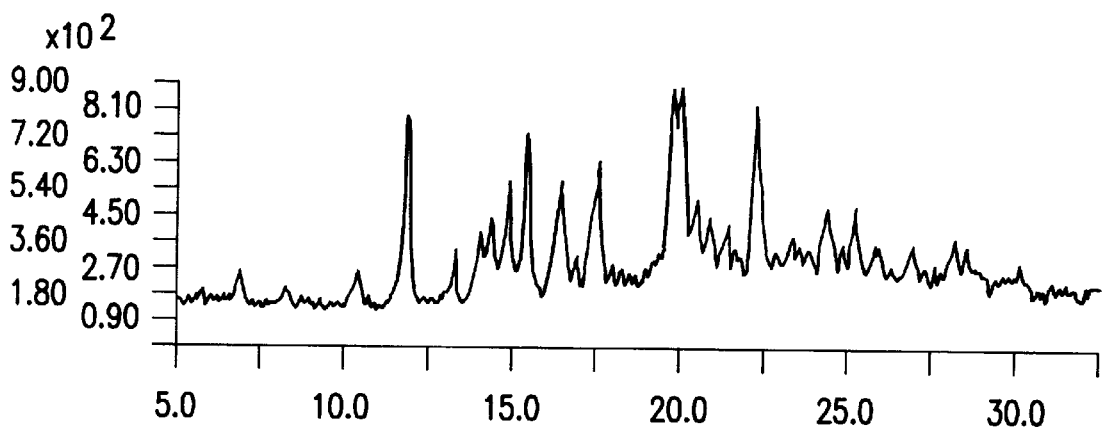

Grams 0.55 g of L-lysine salt of S(+) 2-(3-benzoylphenyl) propionic acid .1/4 H$_2$O (o.p. of the acid>99%) is obtained, melting at 147°–149° C., the X-ray diffraction spectrum of which is shown in FIG. 2.

(H$_2$O)K.F.: 1%+0.3%

$[\alpha]_D$=–0.3° (c=1%, MeOH); $[\alpha]_{436}$=–9.1° (c=1% MeOH)

EXAMPLE 6

S(+) 2-(3-benzoylphenyl)propionic acid D-lysine salt .H$_2$O

Figure 3:
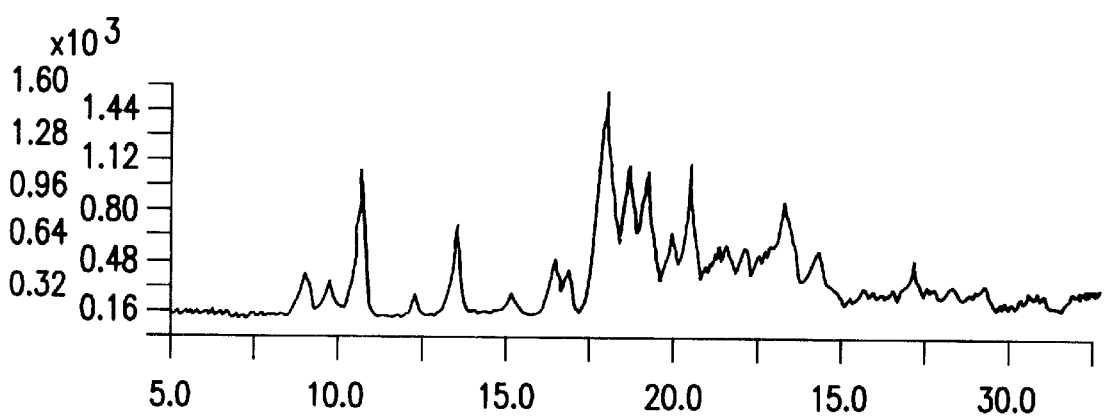

Grams 0.32 of D-lysine monohydrate dissolved at 80° C. in 0.3 ml of distilled water are added under stirring to a solution of 0.5 g of S(+) 2-(3-benzoylphenyl)propionic acid (o.p. >, 90%; $[\alpha]_D$=+50° in dichloromethane) in 5 ml absolute ethyl alcohol. It is diluted with 5 ml of absolute ethyl alcohol under continuous stirring and kept at 0° C. for 5 hours. The precipitate which is formed is filtered and washed with absolute ethyl alcohol. After drying 0.5 g of D-lysine salt monohydrate of S(+) 2-(3-benzoylphenyl) propionic acid (o.p >99%) is obtained, melting at 108°–110° C., the x-ray diffraction spectrum of which is shown in FIG. 3.

(H$_2$O)K.F.: 4%+0.5%

$[\alpha]_D$=–10.1° (c=1%, MeOH); $[\alpha]_{436}$=–29.1° (c=1% MeOH)

EXAMPLE 7

S(+) 2-(3-benzoylphenyl)propionic acid (+) 3-(4phenylpiperazin-1-yl)propane-1,2-diol salt Grams 0.5 of (+) 3-(4-phenylpiperazin-1-yl)propane-1,2-diol are added under stirring to a solution of 0.55 g of S(+) 2-(3-benzoylphenyl)propionic acid (o.p. >90%; $[\alpha]_D$=+50° in dichloromethane) in 5 ml of acetone, heated at about 40°

C. It is left to cool at room temperature to facilitate a slow separation of the salt. After 3 hours a crystalline precipitate consisting of 3-(4-phenylpiperazin1-yl)propane-1,2-diol salt of the S(+) 2-(3-benzoylphenyl) propionic acid (o.p. >99%) and melting at 107°–109° C., is separated by filtration.

[α]$_D$=+20°, 4; [α]$_{436}$=+38°, 9 (c=1% MeOH)

EXAMPLE 8

S(+) 2-(3-benzoylphenyl)propionic acid of (−) 3-(4phenylpiperazin-1-yl)propane-1,2-diol salt Grams 5 of (−) 3-(4-phenylpiperazin-1-yl)propane-1,2-diol are added under stirring to a solution of 0.55 g of S(+) 2-(3-benzoylphenyl)propionic acid (o.p.>90%; [α]$_D$=+50° in dichloromethane) in 5 ml of acetone, heated at about 40° C. It is left to cool at room temperature to facilitate a slow separation of the salt. After 3 hours a crystalline precipitate consisting of 0.67 g of (−) 3-(4-phenylpiperazin-1-yl) propane-1,2-diol salt of the S(+) 2-(3-benzoylphenyl) propionic acid (o.p.>99%) and melting at 118°–120° C., is separated by filtration.

[α]$_D$=+1.2 (c=1% MeOH); [α]$_{436}$=+2.3 (c=1% MeOH)

The crystallographic analysis of the tested compounds has been carried out using a PW1 700 Automated Power Diffratometer System apparatus.

EXAMPLE 9

By re-crystallization from acetone of each of the enantiomerically rich salts obtained according to preparations 1 and 2 the following diastereoisomerically pure salts are obtained:

(2S,2'S) 3'-(4'phenylpiperazin-1'-yl)propane-1',2'-diol 2-(3-benzoylphenyl)propionate, melting at 118°–120° C. [α]$_D$=+1.2° (MeOH);

(2R,2'R) 3'-(4'phenylpiperazin-1'-yl)propane-1',2'-diol 2-(3-benzoylphenyl)propionate, melting at 118°–120° C. [α]$_D$=+1.5° (MeOH);

(2R,2'S) 3'-(4'phenylpiperazin-1'-yl)propane-1',2'-diol 2-(3-benzoylphenyl)propionate, melting at 107°–109° C. [α]$_D$=+20.4° (MeOH);

(2S,2'R) 3'-(4'phenylpiperazin-1'-yl)propane-1',2'-diol 2-(3-benzoylphenyl)propionate, melting at 107°–109° C. [α]$_D$=+20.4° (MeOH).

We claim:

1. S(+) 2-(3-benzoylphenyl)propionic acid (−) 3-(4-phenylpiperazin-1-yl)propane-1,2-diol salt.
2. S(+) 2-(3-benzoylphenyl)propionic acid (+) 3-(4-phenylpiperazin-1-yl)propane-1,2-diol salt.
3. R(−) 2-(3-benzoylphenyl)propionic acid S(−) 3-(4-phenylpiperazin-1-yl)propane-1,2-diol salt.
4. R(−) 2-(3-benzoylphenyl)propionic acid R(+) 3-(4-phenylpiperazin-1-yl)propane-1,2-diol salt.
5. A process for obtaining pure diastereoisomeric salts of (R) or (S) 2-(3-benzoylphenyl)propionic acid with R or S 4-(3-phenylpiperazin-1-yl)propane-1,2-diol by fractional crystallization of the diastereoisomeric mixtures of salts.

* * * * *

UNITED STATES PATENT AND TRADEMARK OFFICE
CERTIFICATE OF CORRECTION

PATENT NO. : 5,808,069

DATED : September 15, 1998

INVENTOR(S) : Bosone et al.

It is certified that error appears in the above-identified patent and that said Letters Patent is hereby corrected as shown below:

```
Title page, Assignee:
Item [73], line 2, delete "Dimpe'" insert therefor
```

-- DOMPE' --

Signed and Sealed this

Twelfth Day of January, 1999

Attest:

*Attesting Officer*

*Acting Commissioner of Patents and Trademarks*

UNITED STATES PATENT AND TRADEMARK OFFICE
CERTIFICATE OF CORRECTION

| | | |
|---|---|---|
| PATENT NO. | : 5,808,069 | Page 1 of 1 |
| APPLICATION NO. | : 08/513842 | |
| DATED | : September 15, 1998 | |
| INVENTOR(S) | : Enrico Bosone et al. | |

It is certified that error appears in the above-identified patent and that said Letters Patent is hereby corrected as shown below:

On the Title Page

Item (73), Assignees, please delete "Dimpe' SpA" and substitute therefor -- Dompé SpA --.

Signed and Sealed this

Twenty-second Day of June, 2010

David J. Kappos
*Director of the United States Patent and Trademark Office*